United States Patent
Geddes et al.

(10) Patent No.: US 7,096,059 B2
(45) Date of Patent: Aug. 22, 2006

(54) DEVICE AND METHOD FOR ELECTROCARDIOGRAPHY ON FREELY MOVING ANIMALS

(75) Inventors: Leslie A. Geddes, Lafayette, IN (US); Candice B. Kissinger, West Lafayette, IN (US); Joseph A. Bougher, Monticello, IN (US); Stephen J. Clevenger, West Lafayette, IN (US)

(73) Assignee: Bioanalytical Systems, Inc., West Lafayette, IN (US)

( * ) Notice: Subject to any disclaimer, the term of this patent is extended or adjusted under 35 U.S.C. 154(b) by 352 days.

(21) Appl. No.: 10/612,126

(22) Filed: Jul. 2, 2003

(65) Prior Publication Data

US 2004/0006280 A1    Jan. 8, 2004

Related U.S. Application Data

(60) Provisional application No. 60/393,738, filed on Jul. 3, 2002.

(51) Int. Cl.
*A61B 5/402*    (2006.01)
(52) U.S. Cl. .................................................. 600/509
(58) Field of Classification Search ........ 600/508–509, 600/576, 581, 573
See application file for complete search history.

(56) References Cited

U.S. PATENT DOCUMENTS 3,817,241 A    6/1974  Grausz
4,380,237 A    4/1983  Newbower
4,413,627 A    11/1983 Schindler
4,432,367 A    2/1984  Piesinger
4,572,206 A    2/1986  Geddes et al.
4,644,960 A    2/1987  Johans
4,813,423 A    3/1989  Miyasaka et al.
4,836,214 A    6/1989  Sramek
4,852,580 A    8/1989  Wood
4,899,759 A    2/1990  Pederson et al.
4,979,510 A *  12/1990 Franz et al. ................. 600/374
5,305,712 A    4/1994  Goldstein
5,480,420 A    1/1996  Hoegnelid et al.
5,549,109 A    8/1996  Samson et al.
6,095,987 A    8/2000  Shmulewitz et al.
6,152,882 A *  11/2000 Prutchi ....................... 600/509
6,445,941 B1   9/2002  Hampton et al.

FOREIGN PATENT DOCUMENTS

DE    43 18 963 C1 *  5/1994
JP    9-206285         8/1997

* cited by examiner

*Primary Examiner*—Carl Layno
(74) *Attorney, Agent, or Firm*—Ice Miller LLP

(57) ABSTRACT

An electrocardiography device and method that is able to obtain the electrocardiogram of a freely moving animal. The device and method utilizes at least two catheters to obtain the electrical signals from the heart of the animal being tested. The catheters are filled with an electrically-conductive, physiological solution and are used in combination with at least two test leads that are able to transfer the electrical signals from the animal to an ECG monitoring device. The device and method also allows for fluids to flow through the catheters to other devices such as a blood sampler controller and/or an infusion pump.

26 Claims, 10 Drawing Sheets

DEVICE AND METHOD FOR ELECTROCARDIOGRAPHY ON FREELY MOVING ANIMALS

CROSS-REFERENCE TO RELATED APPLICATIONS

This application claims the benefit of U.S. Provisional Application No. 60/393,738, filed Jul. 3, 2002.

FIELD OF THE INVENTION

This invention relates to electrocardiography, and, in particular, to a device and method for obtaining electrocardiograms on freely moving animals.

BACKGROUND OF THE INVENTION

An electrocardiograph is essentially a voltmeter or galvanometer which records changing electrical activity in the heart by means of positive and negative electrodes. Electrocardiography is the process of recording the potential differences at these electrodes. An electrocardiogram (hereinafter referred to as an ECG) is a representation on paper, or an oscilloscope display, or a computer screen, of electrical activity in the heart. An ECG is basically obtained by monitoring the voltage changes at electrodes connected to test leads, which leads are, in turn, connected to the electrocardiograph. The electrodes of the test leads can be connected to various regions of the body. In humans, the electrodes are often placed on the chest (precordial chest ECG), while in animals, the electrodes are typically placed on the limbs (body surface limb ECG). Sometimes, electrodes are placed inside the cardiac chambers.

ECGs are used by veterinarians and physicians to diagnose cardiovascular diseases. They also provide a valuable tool for biomedical research, including but not limited to preclinical drug discovery and toxicology studies. When pharmaceutical companies submit new drug applications to regulatory agencies, such as the United States Food and Drug Administration, such agencies often require information about cardiovascular function relative to the introduction of the drug or its metabolites. Drug-induced cardiovascular anomalies revealed in the human population subsequent to the introduction of a new pharmaceutical product can result in the termination of such a product (i.e., the drug will be prohibited by the regulative agency from use in the manner proposed in the application). There is, therefore, a pressing need to develop models for use in drug development that can predict cardiovascular problems in humans prior to use in actual human subjects. Adverse indications involving the heart would ideally be discovered early in the process of discovery, before large research investments had been made in developing the drug candidate.

Laboratory rats and mice are typically the first animals to be exposed to potential drug candidates. Although ECGs are recorded in rats and mice, for several reasons, the rat and mouse are not considered the ideal animal model for cardiovascular screening. With regard to obtaining ECGs from laboratory rats and mice, the following three approaches are typically used: (1) immobilization, (2) telemetry or (3) recording platform. Each of these approaches have shortcomings as is described in greater detail herein.

Immobilization involves connection of electrical leads (e.g. coated copper wire) to the limbs of the rat. The rat must be immobilized during such studies because movement can create signal artifacts attributable to the electrical activity of other muscles. To establish a reliable connection and ensure that the rat's fur does not interfere with the connection, it is necessary to pierce the skin of the rat. The piercing of the rat's skin can be accomplished by the use of hypodermic needles or alligator clips. The rat is often anesthetized or at least restrained during these studies to reduce signal noise due to movement and because the piercing of the rat's skin can be painful.

The immobilization technique, thus, results in several shortcomings. The ECGs obtained are those of an immobilized animal that may reflect restraint stress in those ECGs as well as other physiological indicators. If anesthetic is used to accomplish the restraint, the ECGs represent a cardiovascular system under the influence of another variable and may not accurately portray the effect of the drug on the cardiovascular system. Both the immobilization and the presence of anesthesia affect heart rate and therefore can affect the resulting ECG. The anesthetized animal may behave differently according to the uptake and/or clearance of the drug, because drug uptake by tissues and clearance from tissues is often through the blood stream and the rate of blood flow is governed by the heart rate. Drug-induced changes in electrocardiograms may be associated with delayed metabolism and/or clearance of a drug, as in the case of terfenadine, a drug strongly associated with the cardiovascular anomaly known as QT interval prolongation. If an anesthetic is used instead of a restraint, there still could be an effect on body temperature because certain anesthetics can lower body temperature. Body temperature is another variable that affects drug uptake, clearance, and general metabolism. Larger animals require larger and sturdier restraints to effectively prevent movement. In many breeds of dog, it is sufficient for a practitioner to hold the dog on an examining table. With other large animals, a strong restraint is necessary. It is therefore desired to provide a device and method for electrocardiography that can be used on animals of all sizes (mouse, rat, dog, monkey, and even a human) that at least does not require that the animal be anesthetized, and, in the case of rodents or other small animals, does not require that the animal be restrained.

The telemetry method of cardiovascular screening in rats requires that deep body surgery be conducted to open the body cavity for implantation of a small, battery-powered and sterile transmitter into the rat. To detect electrical activity in the heart, leads from the transmitter are attached to the rat's heart or blood vessels adjacent to the heart. Before using the rat with such an implant for research and testing, the rat requires several days of recovery after the surgery. After such recovery, the rat can be allowed to move without restraint within a specialized cage and tests, such as an ECG, can be taken on the freely moving rat.

The telemetry device and method for electrocardiography has several shortcomings. The battery in the transmitter has a finite lifetime, thereby limiting the amount of time and number of ECGs that can be obtained from the subject rat. The rat is exposed to a magnetic field that induces the battery to turn on and induces the transmitter to send signals to a receiving antenna. The battery is turned off by a subsequent pulse of the magnetic field. By judicious use of these fields, the battery lifetime is somewhat conserved, but the scope of the research is necessarily constrained by the lifetime of the battery. The telemetry approach is also very sensitive to magnetic fields that are not part of the equipment, which cause problems with the operation of the battery. Likewise, the telemetry approach is sensitive to transmitter/receiver systems from adjacent animal studies, which interfere with the collection of the signals from the animal. Thus, animals with these implants need to be kept close to the antennas to ensure that the information is properly collected and need to be isolated from one another to ensure that the transmission of the electrocardiography signals do not interfere with one another. The need for proximity to the receiving antenna, the sensitivity of the antenna to stray radiofrequency interference and the susceptibility of the battery to other magnetic fields, all contribute to a burden on the research facility. Moreover, the need for deep body surgery to implant the transmitter and the subsequent recovery time place a strain on the animal and increase the risk of infection. Therefore, it is desired to provide a device and method for electrocardiography that does not require intensive, deep body surgery and is not constrained by the manner of limitations imposed by the use of a battery and antenna.

The use of a recording platform for obtaining ECGs in mice is a relatively new approach. This approach does not require that the mouse be restrained, as in the immobilization method, and does not require surgery to implant a device, as in the telemetry method. The recording platform is permeated with electrodes. When a mouse is placed on the platform and has all of its paws in direct contact with these electrodes, a signal is obtained that can be viewed on a computer screen and recorded. The platform is typically elevated and the mouse must be monitored by a technician who triggers the recording of the ECG once the technician detects a usable signal on the computer screen. These platforms are manufactured under the name AnonyMOUSE™ by Mouse Specifics, Inc. The recording platform has the advantage of being non-invasive (no surgery required) and is not painful to the animal since no leads must be attached to the skin. However, the use of a recording platform has several shortcomings.

The primary shortcoming is that the recording platform requires the animal to remain still and in contact with the leads for acquisition of a signal to produce an ECG. A rearing animal, for example, would not produce a useable signal. Further, because the animal is not contained, there is a risk of escape or injury to the animal if it leaps from the elevated platform. If the animal was contained within cage walls to prevent this risk, it would be able to rear and lean on the cage walls, resulting in a loss of signal and intermittent electrocardiograph readings. Finally, the animal must be handled in order to be transferred from its home cage to the recording platform, and some amount of time would be required to allow the animal to return to resting status after the stimulus of handling. Accordingly, it is desired to provide a device and method for electrocardiography on freely moving animals that does not require handling of the animal, does allow for containment of the animal, is not affected by normal behavior such as rearing, and is not limited by intermittent electrocardiograph readings (as results from the required contact of the animal's paws to the elevated platform on the recording platform technique). It is also desired that the acquisition of recordings be independent of human intervention rather than requiring monitoring by a technician as in this recording platform technique.

A few other points specific to electrocardiography in animals are worthy of note. Surface ECGs are normally obtained by connecting an electrically conductive test lead to the skin, often in combination with an electrically-conductive gel to improve electrical contact between the wires in the lead and the skin. This technique must be modified for animals that have a thick fur coat since the hairs of the fur coat can prevent complete contact between the test lead and the skin. Shaving of the fur may be insufficient to make these connections as the fur cannot always be shaved close enough to completely remove the hair without also damaging the skin. For humans, to get good contact, electrically conductive gels are used to make contact with the skin. Animals, such as most breeds of dogs, can be monitored using devices which pinch deep into the skin, such as alligator clips, because they are tolerant of the discomfort of using this method. Other animals, such as rats, are intolerant of such methods and must be anesthetized or restrained in tubes or other devices which prevent them from moving in response to the discomfort of the measurement technique. During even short periods of restraint, such animals are stressed significantly, resulting in changes to their heart rate, blood pressure, circulating concentrations of stress hormones, and metabolic parameters. Neither a restrained animal, nor an anesthetized animal, is representative of normal physiology. It is therefore desired to provide a device and method for electrocardiography that can be used on various types of animals without restraint, the use of anesthetic, the requirement to shave the animal, or the use of conductive gels.

BRIEF SUMMARY OF THE INVENTION

The present invention comprises a method and device used to obtain ECGs from freely moving animals. The method of the present invention expands on the utility of the implementation of intravenous catheters. Catheters are hollow and typically flexible tubes that can be placed in a vein or an artery for the purpose of allowing fluids to be injected into the body or for the purpose of withdrawing fluids from the body.

According to the present invention, the catheters can be used as electrical connections to the heart to obtain ECGs. In the present invention, a catheter is placed into a vein or artery and then filled with a physiological solution. The solution acts as a barrier to prevent blood from entering the catheter and clotting between sampling or infusion events. The presence of such a solution makes a catheter conductive to electrical signals. Thus, when the catheters are inserted into the veins in a position that is close to either end of the heart, without actually entering the heart, the catheters can behave as internal test leads for an ECG monitoring device. Because it is also desired to be able to continue to sample blood and/or infuse a drug or drugs during the collection of electrocardiograms, the invention also includes the means of connecting these fluid-filled catheters to the ECG monitoring device and maintaining free flow of fluid to other devices such as a blood sampler controller and/or an infusion pump.

One embodiment of the present invention provides for an electrocardiography device having a movement responsive caging system, an automated blood sampler controller, an ECG monitoring device, a first and second catheter connected to a first and second test lead, respectively, and a reference lead. The first and second catheters are used to carry blood and/or solution to and from an animal and the first and second test leads are used for transmission of the electrical signals from the animal that comprise the ECG of that animal. The reference lead is connected to the animal by a surgical staple. In this embodiment, the animal is contained within a movement responsive caging system to ensure that the animal can move around freely without being constantly monitored by a human attendant. In addition, the movement responsive caging system enables both electrical and fluid connections to be made between the animal and a device outside of the cage without using swivel-commutators. Therefore, test leads, such as wires and tubing, remain contiguous and suffer no signal degradation due to commutator deficiencies and no exposure to additional dead volume or non-sterile surfaces due to the use of liquid swivels. The blood sampler controller controls the bidirectional flow of fluid through the first and second catheters and the ECG monitoring device collects the electrical signals of the first and second test leads and the reference lead. In this manner, the first and second test leads are able to provide a mechanism for picking up the electrical signal flowing through the first and second catheters, while allowing the catheters to be filled with a solution. The electrocardiography device of the present invention can further comprise a printer and/or a display, a computer, and a remote computer. All of these devices can be operatively connected to the blood sampler controller and/or the ECG monitoring device. A user of these devices can obtain an ECG of an animal before and after exposure to a drug, and simultaneously collect blood to correlate drug concentrations with ECG events.

Several embodiments of a test lead exist that can be used in the present invention. One exemplary embodiment of the test lead comprises an extender wire, a hollow tube, a flexible wire, a heat shrink tubing, and a socket connection. The extender wire comprises an electrically conductive material. Examples of other embodiments of such test leads include: (1) a test lead that utilizes a metal coated inside portion of a catheter, instead of an extender wire; and (2) a test lead that utilizes a catheter with a conductive coating and a ground wire on the outside surface of the catheter, instead of a extender wire.

The method of the present invention for obtaining the ECG of an animal exposed to a drug includes the following steps. First, the first and second catheters are inserted into the jugular vein and femoral vein, respectively, of the animal. The first and second catheters are connected to the first and second test leads, respectively, and are filled with an electrically conductive, physiological solution to permit transmission of electrical signals from the animal to the first and second test lead. The reference lead is connected to a surgical staple on the animal's back. The user can use the ECG monitoring device to process the signals gathered by the first and second test leads in order to obtain the ECG of the animal. In one embodiment, the drug to be studied is then added to the solution to determine the effects of the drug on the heart of the animal. The ECG monitoring device processes the signals received from the first and second test leads and transfers the information to the computer and/or the printer/display unit.

BRIEF DESCRIPTIONS OF THE DRAWINGS

DESCRIPTION OF THE INVENTION

Figure 1:
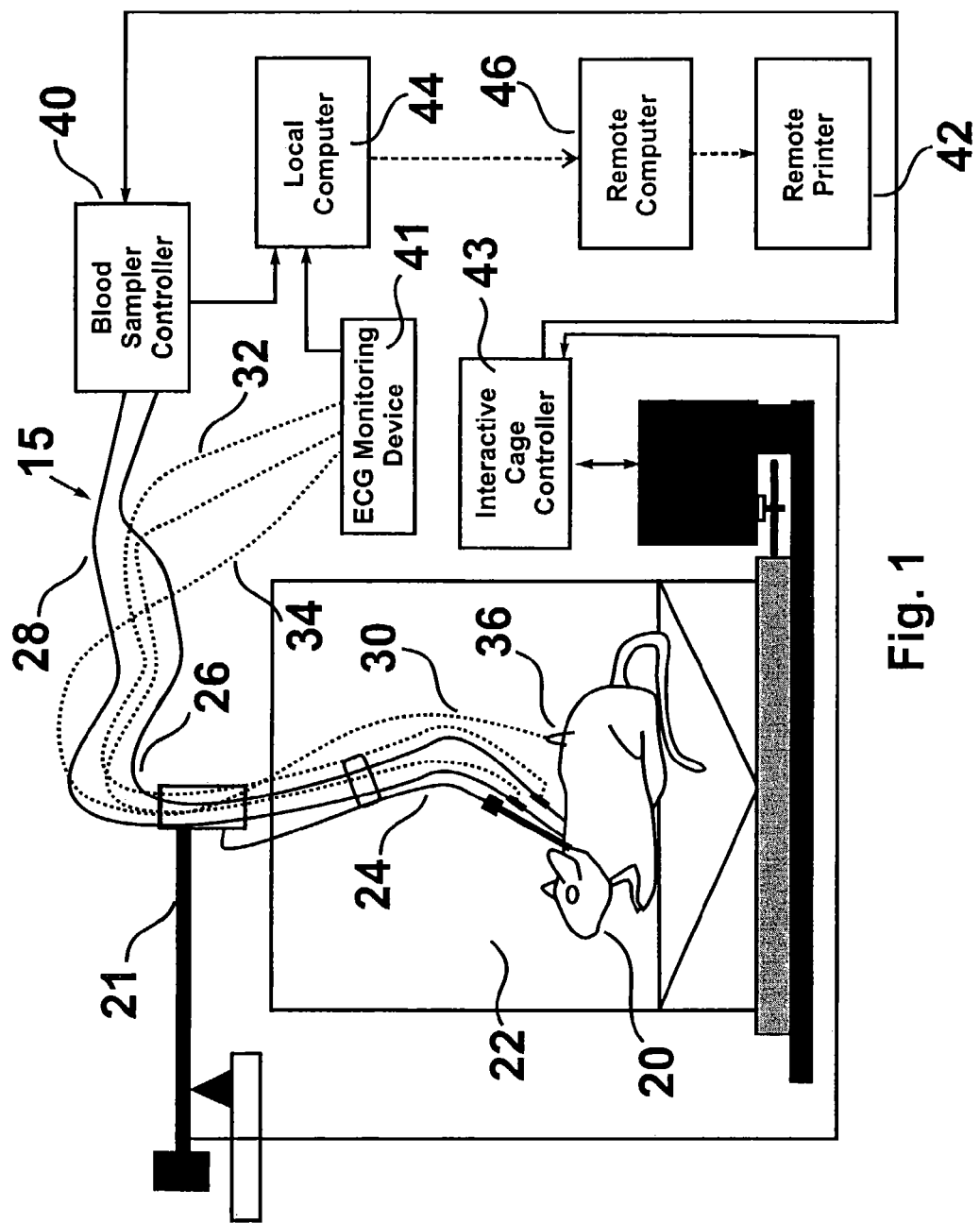
FIG. 1 shows a block diagram of an exemplary embodiment of the present invention with a movement responsive caging system and a blood sampler controller.

The present invention comprises a method to obtain ECGs from animals. As used herein, the term "animal" encompasses all mammals for which it is desired to obtain at least one ECG. Hence, the term "animal" includes laboratory animals, such as mice, rats, dogs, monkeys, other primates, guinea pigs, gerbils, hamsters, sheep, and pigs. The term "animal" also includes humans. The present invention also comprises a device to facilitate this method.

The method of the present invention expands on the utility of the implantation of intravenous catheters in laboratory animals. Catheters are hollow and typically flexible tubes that are used to conduct fluids from within the body to outside of the body, or vice versa. When placed in veins, or arteries, catheters are generally used to: (a) remove blood samples; (b) introduce liquid solutions of drugs or other substances into the blood stream via infusion; or (c) introduced solutions and then subsequently remove a sample of body fluid from the same catheter. In addition to placement in blood vessels, catheters can be placed into other body spaces, such as the bile duct, spinal column, urinary tract, tear ducts, or vessels in the brain.

Animals placed in an blood sampler controller, such as the automated blood sampler disclosed in U.S. Pat. No. 6,062,224, may have catheters placed in both the right jugular vein and the left femoral vein. While one vein is used for blood sampling (e.g. jugular vein), the other vein is used for drug infusion (e.g. femoral vein), or vice versa. This arrangement places the catheter on an axis running diagonally across the heart from one atrium (left or right) to a position just below the opposite ventricle (left or right), respectively. The functions of blood sampling and drug infusion are usually separated by the use of two different catheters to avoid contamination of blood with the drug being infused into the animal.

According to the present invention, these existing catheters are used as electrical connections to the heart. Catheters used to collect blood, or infuse fluids, must be filled with a physiological solution between uses. The filling solution acts as a barrier to prevent blood from entering the catheter between sampling or infusion events. Without such a barrier, blood would fill the catheter and then clot, preventing subsequent delivery of fluid or withdrawal of blood through the catheter. The presence of a physiological solution, such as 0.9% sodium chloride, also makes the catheter conductive to electrical signals. Veins empty into the atrium of the heart, but catheters placed into those veins can be positioned so that they are close enough to either end of the heart without having to enter the heart itself. Since the jugular vein empties into one end of the heart near the atrium, and the femoral vein empties into the vena cava behind and at the other end of the heart (near the ventricle), these two catheters can behave as internal test leads when connected to an ECG monitoring device. However, fluid-filled test leads are far less conductive than electrical wires and involve high resistance to the flow of the electrical current. Thus, this approach is counter intuitive to conventional wisdom of those involved with electrocardiography. Typically, electrical connections in electrocardiography involve electrodes and wires which are as electrically conductive as possible to avoid impedance of the signal by resistance to the flow of the electrical current through the test lead. The need for low resistance is further demonstrated by the use of electrically conductive gels which make contact between leads and skin in typical electrocardiograph experiments in humans and other certain animals. The high resistance of the fluid-filled test leads must be overcome through careful modification and balancing of the leads and the input stage of the amplifier used in the ECG monitoring device. Because it is also desired to be able to continue to sample blood and/or infuse a drug or drugs during the collection of ECGs, the invention also includes a means of connecting these fluid-filled catheters to the ECG monitoring device and maintaining free flow of fluid to other devices such as a blood sampler controller and/or an infusion pump.

This embodiment of the invention as described for rats can be used with a movement responsive caging system, as disclosed in U.S. Pat. No. 5,816,256, and/or an automated blood sampler, as disclosed in U.S. Pat. No. 6,062,224. When used with other rodents, these same devices can be used. When used for larger animals, such as a pig, another arrangement would be used to restrict, but not restrain, the animal's movement and to protect the test leads.

Figure 2:
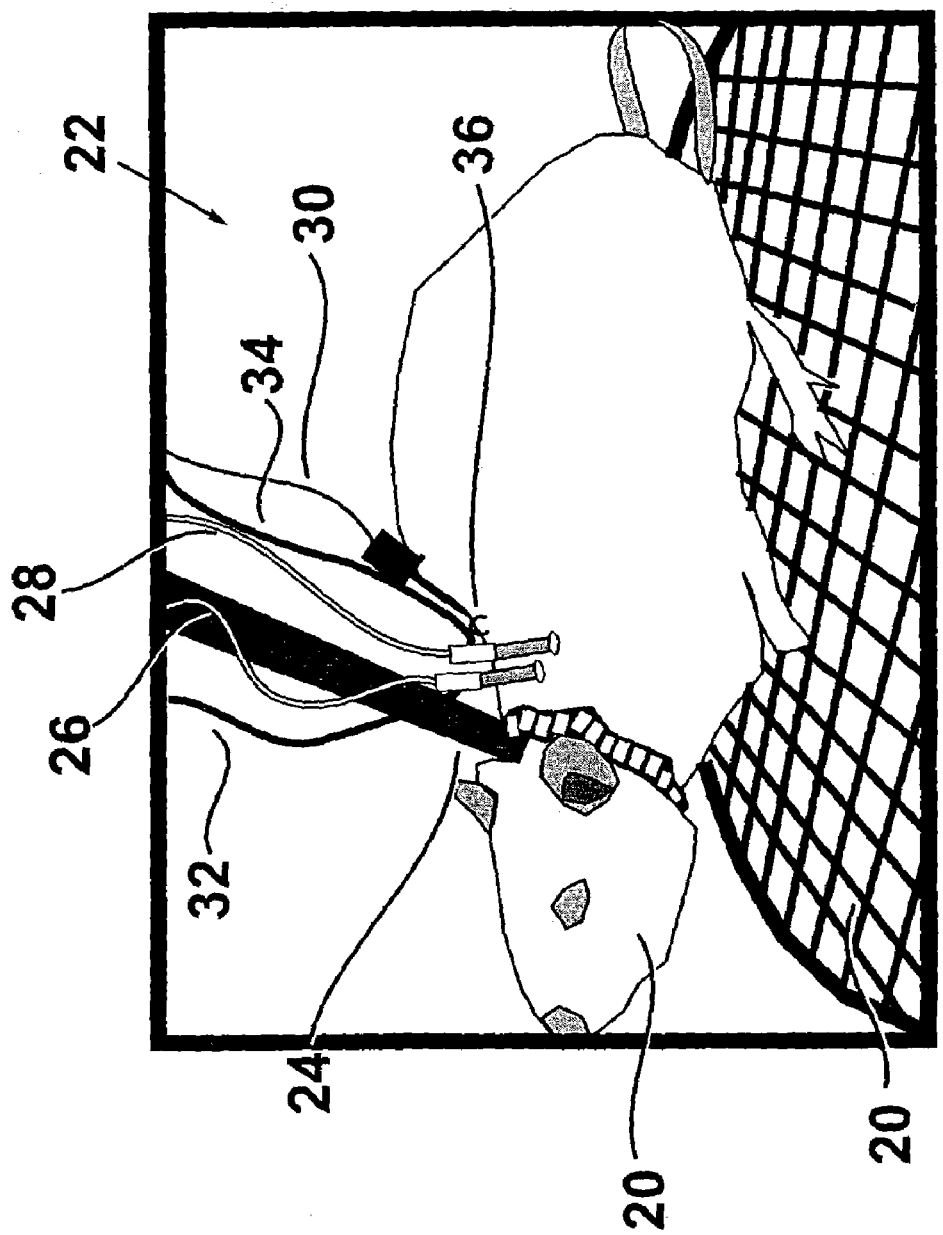
FIG. 2 shows a close-up view of the movement responsive caging system with a rat having the exemplary embodiment of FIG. 1 connected thereto.

FIG. 1 shows a block diagram of one exemplary embodiment of the present invention. As shown in FIG. 1, this embodiment comprises an electrocardiography device 15 that utilizes a movement responsive caging system 22. In this embodiment, movement responsive caging system 22 is of the type disclosed in U.S. Pat. No. 5,816,256. FIG. 2 shows an isolated view of a rat 20 in movement responsive caging system 22. Referring to FIGS. 1 and 2, rat 20 is tethered to a movement-responsive mechanism control 21 (shown in FIG. 1) of caging system 22 by a tether 24. Rat 20 has connected to it a first catheter 26, a second catheter 28, and a reference lead 30. First catheter 26 is connected to a first test lead 32 and second catheter 28 is connected to a second test lead 34. While first and second catheters 26 and 28 are used to carry blood and/or solution to and from rat 20, first and second test leads 32 and 34 are used for transmission of the electrical signals from rat 20 that comprise the ECG of rat 20. Reference lead 30 is connected to rat 20 by a surgical staple 36 placed somewhere on the back of rat 20. Thus, in this embodiment, electrocardiography device 15 comprises first and second catheters 26 and 28, first and second test leads 32 and 34, reference lead 30 and movement responsive caging system 22. As is explained in greater detail herein, the movement responsive caging system is not required but provides several advantages.

Referring still to FIG. 1, electrocardiography device 15 further comprises blood sampler controller 40 and an ECG monitoring device 41. Controller 40 is operably connected to first and second catheters 26 and 28 in order to control the bidirectional flow of fluid through first and second catheter 26 and 28 in a manner known in the art. For example, with regard to the control of fluid in first and second catheters 26 and 28, controller 40 may comprise the automated blood sampler of U.S. Pat. No. 6,062,224, which is available from Bioanalytical Systems, Inc. of West Lafayette, Ind., United States of America. In this embodiment, controller 40 is dedicated to the collection of blood from and delivery of saline to one of the first and second catheters 26 and 28.

As shown in FIG. 1, ECG monitoring device 41 is operably connected to first and second test leads 32 and 34 and reference lead 30 in order to collect the electronic signals that comprise the ECG of rat 20. Controller 40 and ECG monitoring device 41 may be connected or networked together to coordinate the movement of the fluids through first and second catheters 26 and 28 with the collection of electrical signals from first and second test leads 32 and 34 and reference lead 30. While ECG monitoring device 41 and controller 40 are two separate devices in this exemplary embodiment, it will be appreciated by one skilled in the art that a single control device or multiple control devices can collect the electronic signals and control the flow of fluid through the catheters. For example, controller 40 could collect the electrical signals of first and second test leads 32 and 34 and reference lead 30, thereby eliminating the need for a separate ECG monitoring device 41.

Referring to FIG. 1, in this embodiment, electrocardiography device 15 further comprises a remote printer 42, a computer 44, an interactive cage controller 43 and a remote computer 46. Printer 42 is operably connected to remote computer 46, and remotely connected to controller 40, ECG monitoring device 41 and to local computer 44. Interactive cage controller 43 controls the movement of movement responsive caging system 22 and is operably connected to controller 40.

Local computer 44 includes a storage device and is operably connected to controller 40, printer 42 and remote computer 46. The connections of controller 40, printer 42, interactive cage controller 43, local computer 44, and remote computer 46 are achieved by interconnectivity mechanisms well known in the art, including, but not limited to, serial connection, parallel connection, use of a bus, ethernet, internet, Appletalk or other network, radio frequency, microwave, or Internet. The salient feature of each operative connection between these devices is that it is able to transmit and/or receive the data appropriate to the device at a speed sufficient for operational use of the device and in a manner that does not interfere with other devices in proximity to that device. For example, the connection between remote computer 46 and printer 42 may comprise RS-232 serial or USB connection, for limited packages of data are exchanged and the devices can be located in proximity to each other. The connection between local computer 44 and controller 40 may be an electrical bus as more data is exchanged and the devices can be in proximity to each other. The connection between local computer 44 and remote computer 46 may be over the Internet to accommodate the remote location of remote computer 46.

Printer 42 serves as an output device for displaying information collected by controller 40, ECG monitoring device 41, local computer 44 and/or remote computer 46. It will be appreciated by those of skill in the art that the output device can comprise printer 42 or, alternatively, can comprise a display mechanism to display the output from controller 40, ECG monitoring device 41, local computer 44 and/or remote computer 46. Moreover, it will be appreciated by one skilled in the art that the output device may be connected to controller 40, ECG monitoring device 41, and/or local computer 44 for printing and/or displaying the information available to each of these devices. This output device can comprise any number of mechanisms that are able to print and/or display the electrical signals of test leads 32 and 34 and reference lead 30 including, but not limited to, a video display, a flat-panel display, a LCD display, a thermal printer, a matrix printer, or a laser printer.

Local computer 44 operates in cooperation with controller 40 for data collected by controller 40. In this embodiment, such data includes data related to the flow of fluid in first and second catheters 26 and 28. Computer 44 further operates in cooperation with ECG monitoring device 41 for data collected by electrical signals of first and second test leads 32 and 34 and reference lead 30. While controller 40, printer 42, ECG monitoring device 41 and local computer comprise multiple devices in this embodiment, it will be appreciated by those of skill in the art that they all may comprise a single device. For example, a single personal computer having a video display and a printer attached thereto and having a specialized controller card inserted into the bus of the computer can accomplish the objectives of each of these devices.

Remote computer 46 may be located away from the laboratory, and hence, away from controller 40, ECG monitoring device 41, and rat 20. In this manner, the data of controller 40 and ECG monitoring device 41 may be viewed remotely and controller 40 may be controlled remotely by remote computer 46. It will be appreciated by those of skill in the art, that the system of the present invention need not include local computer 44 and printer 42. Instead, remote computer 46 may work directly with controller 40 and ECG monitoring device 41.

In the embodiment of FIGS. 1 and 2, first and second catheters 26 and 28 are inserted into the jugular vein and femoral vein, respectively, of rat 20 by methods well known in the art. Alternately, first catheter 26 could be inserted in the femoral vein and second catheter 28 could be inserted into the jugular vein. ECG monitoring device 41 is able to process the signals of first and second test leads 32 and 34 in either orientation. First and second catheters 26 and 28 are filled with an electrically conductive, physiological solution to permit the transmission of electrical signals from rat 20 to first and second test leads 32 and 34. Such solutions include but are not limited to saline, Ringer's solution, and blood (with or without anticoagulants). These solutions have a chemical composition similar to body fluids and do not cause harm, pain, distress, or physiological imbalance in the animal. The solution may be modified by the addition of one or more drugs whose effect(s) on the heart of rat 20 are to be studied.

Figure 3:
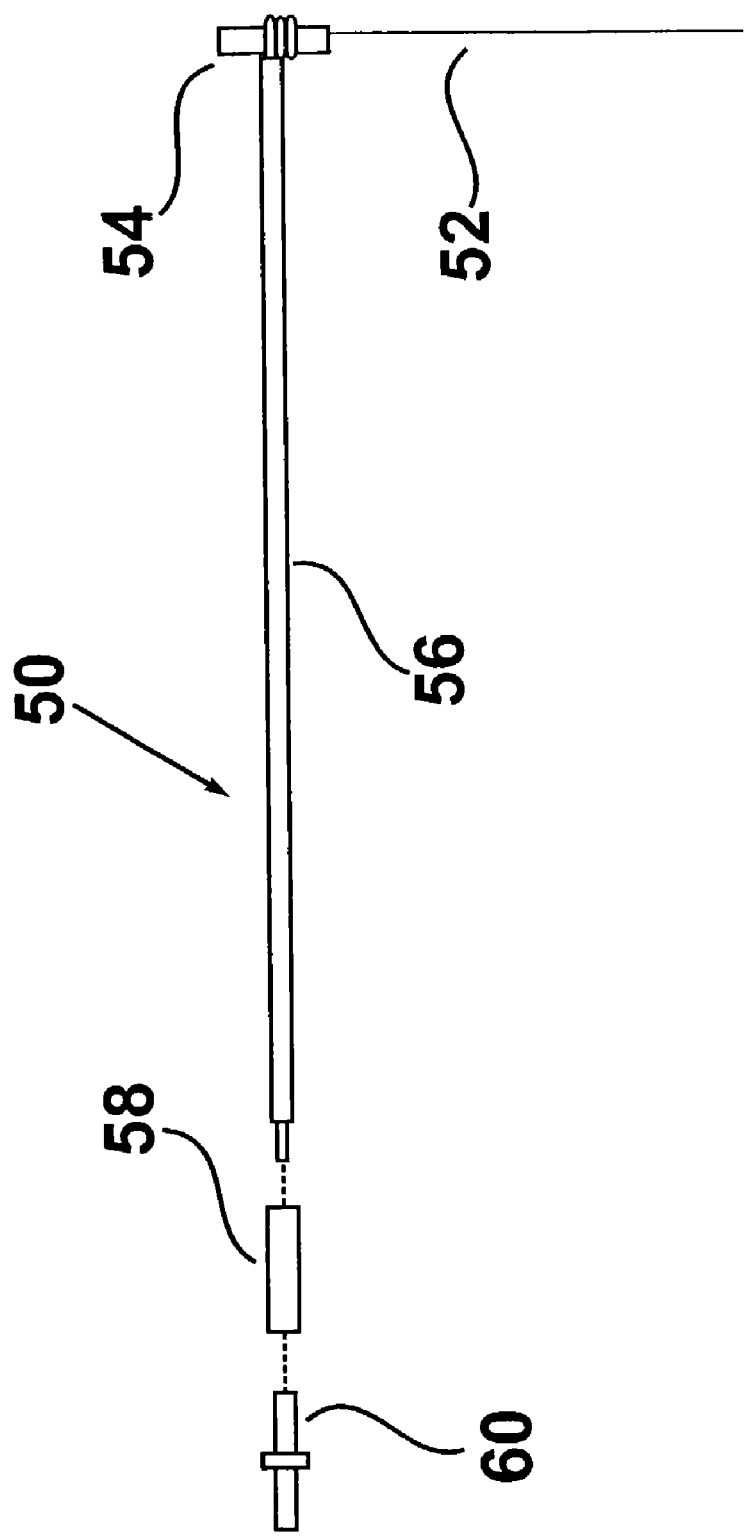
FIG. 3 shows a diagrammatic view of one embodiment of a test lead that can be used in the present invention.

FIG. 3 shows a diagrammatic view of one embodiment of a test lead that may be used in the electrocardiography device of the present invention. This embodiment, and the embodiments of FIGS. 4–7, provide a mechanism for picking up the electrical signal flowing through first and second catheters 26 and 28. As shown in FIG. 3, first and second test leads 32 and 34 can comprise test lead 50. Test lead 50 comprises extender wire 52, hollow tube 54, flexible wire 56, heat shrink tubing 58, and socket connection 60. Extender wire 52 is comprised of an electrically conductive material such as metals, oxides, amalgams or flexible and conductive polymers or composite materials. Extender wire 52 is inserted into the hollow catheter through which solution may flow. For this reason, the selection of the material of extender wire 52 may be influenced by the particular solution that flows through the catheter. While any electrically conductive material may be used for extender wire 52, one skilled in the art will realize that when certain materials are utilized, the materials may cause desirable or undesirable reactions with the solution that flows through the catheter. For example, stainless steel may produce ferrous salts and silver may produce chloride salts which enhance its use as an electrode, when placed in a saline solution. In contrast, platinum and gold are generally nonreactive to most solutions of the type to flow through the catheter.

In this embodiment, extender wire 52 is electrically connected to tube 54. Tube 54 is adhered to the top of the catheter so that extender wire 52 extends into the catheter. In this embodiment, tube 54 is made of electrically conductive material. Due to the fact that tube 54 can also be in contact with the solution flowing through the catheter, the selection of the electrically conductive material from which tube 54 is made is also influenced by the solution. Possible materials for tube 54 include, but are not limited to, platinum, silver, gold, stainless steel, or other metals, oxides, salts, or amalgams. It will be appreciated by those of skill in the art that various mechanisms may be used to adhere tube 54 to the catheter. For example, tube 54 can reside inside or outside the catheter and be held in place by clamps or sleeves. The holding mechanism chosen should be impervious to fluid flow to prohibit leakage of the solution within the catheter and tube 54 to the outside thereof.

Figure 10:
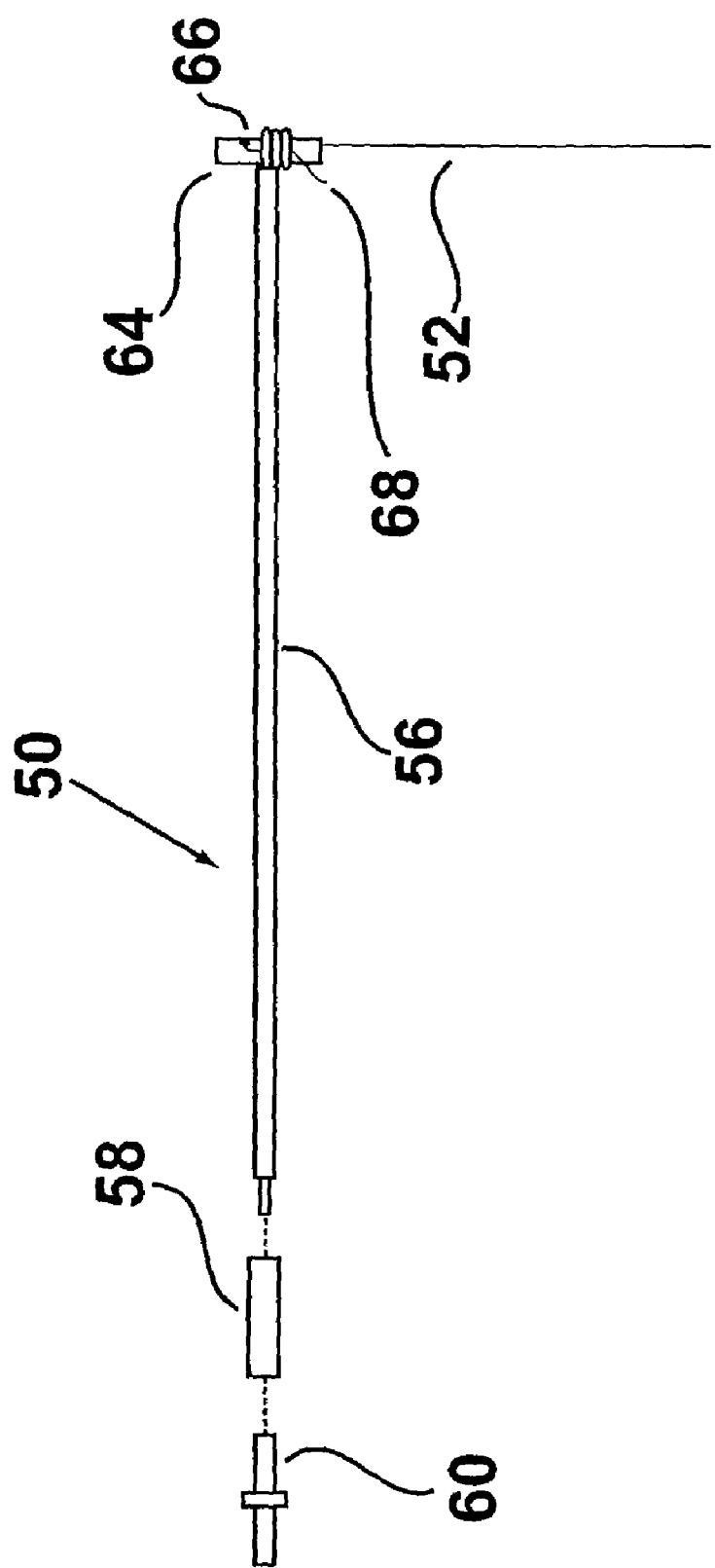
FIG. 10 shows a diagrammatic view of the exemplary embodiment of the test lead of FIG. 3 utilizing a nonconductive hollow tube.

Test lead 50 also includes flexible wire 56. Flexible wire 56 is of a length sufficient to extend from rat 20 to ECG monitoring device 41. Flexible wire 56 comprises electronically-conductive material having insulating material surrounding the conductive material to protect the electrical signal transmitting therethrough. In this embodiment, flexible wire 56 comprises copper wire having an insulative plastic coating. At its first end, the conductive part of flexible wire 56 is connected to tube 54 and extender wire 52 to create electrical contact therewith. Such connection may be made by crimping, soldering, conductive epoxy, or other means known in the art, alone or in combination. It will be appreciated by one skilled in the art that the hollow tube can also be made up of any type of nonconductive materials with a conductive connecting wire placed on or through the hollow tube. For example, FIG. 10 shows a block diagram of test lead 50 with a nonconductive hollow tube 64. Tube 64 has a hole 66 in its side and a connecting wire 68 that passes through the hole 66. In this embodiment, connecting wire 68 is electrically connected to extender wire 52. Connecting wire 68 passes through hole 66 and is electrically connected to the first end of the flexible wire 56 by one of the means described above. In this manner, connecting wire 68 creates electrical contact between flexible wire 56 and extender wire 52.

Referring to FIGS. 3 and 10, at its second end, flexible wire 56 is electrically connected with socket connection 60 by use of heat shrink tubing 58. Heat shrink tubing 58 comprises insulative material and socket connection 60 is comprised of conductive material, such as, gold-coated brass. The purpose of heat shrink tubing 58 and socket connection 60 is to electrically connect flexible wire 56 to ECG monitoring device 41 or to longer electrical leads extending to ECG monitoring device 41. It will be appreciated by one skilled in the art that other electrical connecting mechanisms may be used and are contemplated to be within the scope of the invention. It will also be appreciated by one skilled in the art that more than one flexible wire can be used to connect tube 54 to ECG monitoring device 41.

Figure 4:
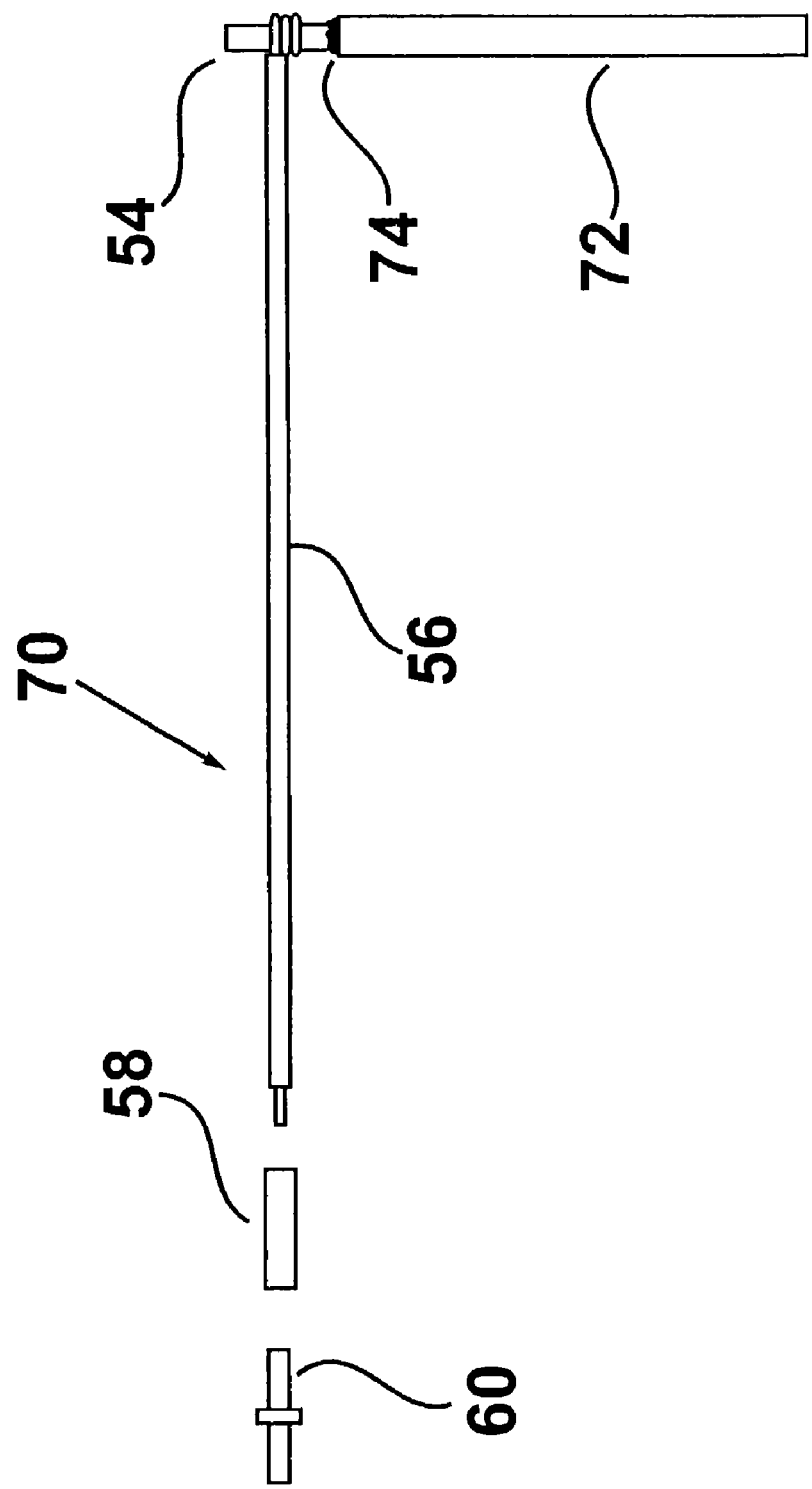
FIG. 4 shows a diagrammatic view of a second embodiment of a test lead that can be used in the present invention.

FIG. 4 shows a second embodiment of a test lead 70 that can be used as first and second test leads 32 and 34 in the present invention. As shown in FIG. 4, test lead 70, like test lead 50, comprises hollow tube 54, flexible wire 56, heat shrink tubing 58, and socket connection 60. However, instead of using an extender wire for extension into the catheter and collection of the signals from rat 20, test lead 70 has a catheter portion 72, extending from hollow tube 54 to rat 20. Catheter portion 72 comprises a catheter tube having a coating of metal on the inside surface thereof. Catheters of this type are available commercially, such as the custom coated polymeric tubing offered by AgION, Inc. of Wakefield, Mass. To attach conductive catheter portion 72 to tube 54, a conductive epoxy 74 is used on the inside of catheter portion 72 and outside of tube 54.

Figure 5:
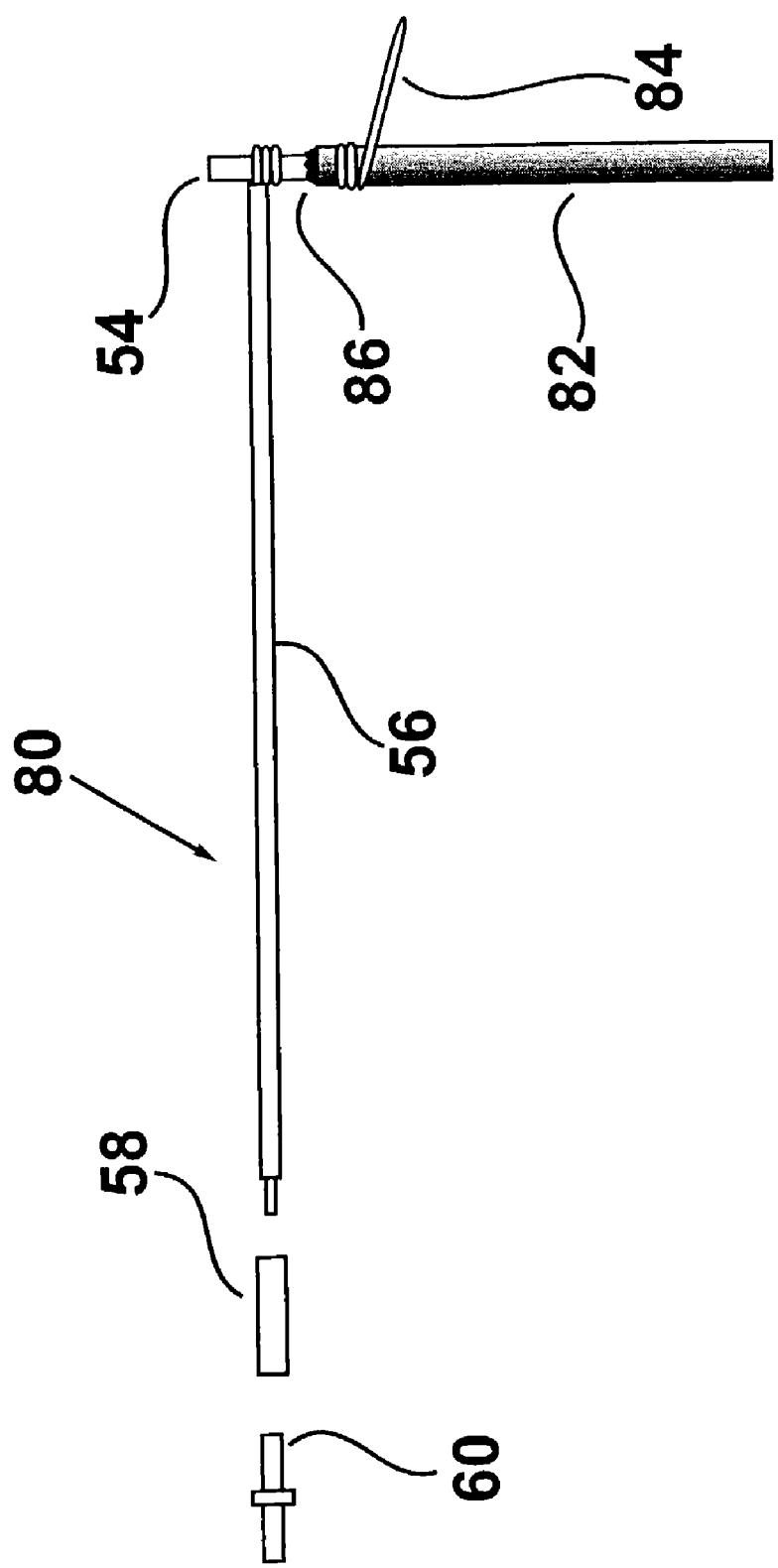
FIG. 5 shows a diagrammatic view of a third embodiment of a test lead that can be used in the present invention.

FIG. 5 shows a diagrammatic view of another embodiment of a test lead 80 that can be utilized as first and second test leads 32 and 34 in the present invention. As shown in FIG. 5, test lead 80 comprises hollow tube 54, flexible wire 56, heat shrink tubing 58, and socket connection 60. Test lead 80 further comprises a catheter portion 82 that extends from hollow tube 54 to rat 20. Catheter portion 82 comprises a catheter tube having a conductive coating on the outside surface thereof. It will be appreciated by one skilled in that art that any number of conductive coatings can be used to create catheter portion 82, including but not limited to, silver metal. Catheters with conductive coatings of this tubing are available commercially, such as the custom-coated catheters and stents made by Spire Corporation. Test lead 80 further comprises a ground wire 84 made of conductive material. Catheter portion 82 is connected to tube 54 by a non-conductive epoxy 86. In the embodiment where tube 54 is made of a nonconductive mater, the non-conductive epoxy 86 would not have to be used and the tube 54 could be connected to catheter portion 82 by any of the mechanisms described herein. Ground wire 84 is wrapped around the conductive outside of catheter portion 82 at one end and connected to the driver lead on ECG monitoring device 41 at its other end. In this embodiment, ground wire 84 replaces reference lead 30 and surgical staple 36 described in association with FIGS. 1 and 2.

Figure 6:
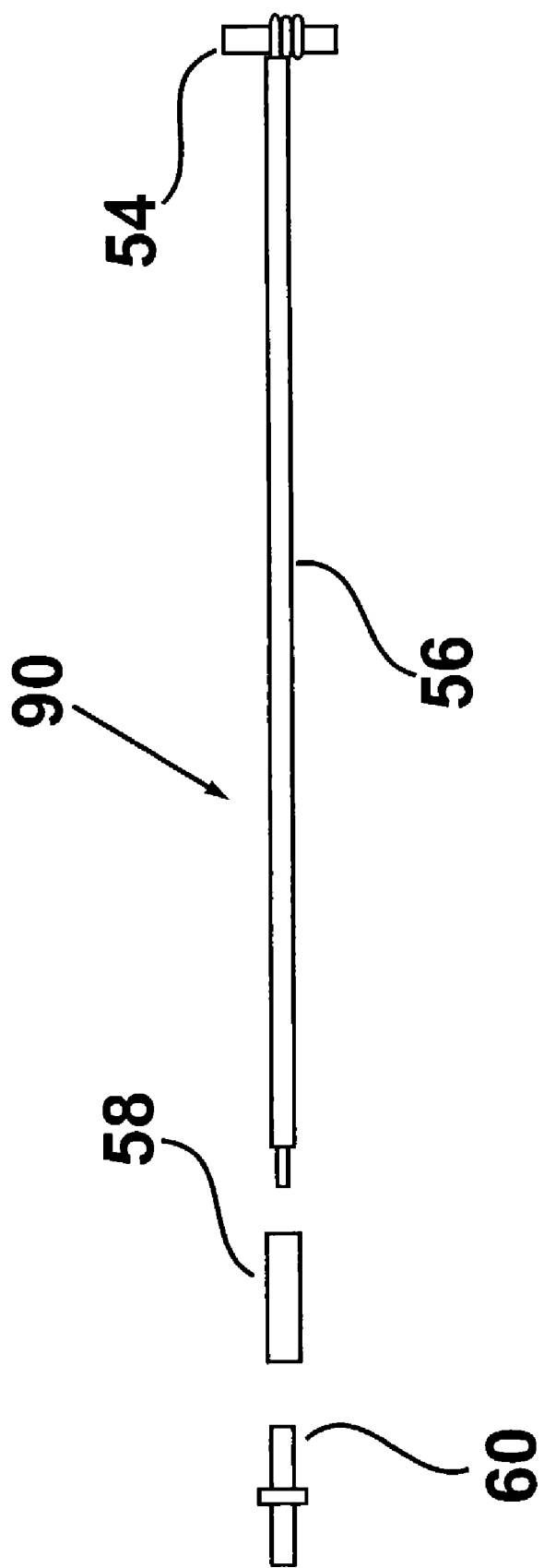
FIG. 6 shows a diagrammatic view of a fourth embodiment of a test lead that can be used in the present invention.

FIG. 6 shows yet another embodiment of a test lead 90 that can be used as first and second test leads 32 and 34 in the present invention. As shown in FIG. 6, test lead 90 only comprises tube 54, flexible wire 56, heat shrink tubing 58, and socket connection 60. No extenders in or through the catheter are provided. This has utility when the electrical signal in the catheter portion extending from tube 54 to rat 20 is of sufficient quality and strength that a conductive material is not necessary to be used in association with the catheter and the solution it contains. The quality and strength of the signal depends on the proximity of the catheter to the signal generator (the heart), the solution within the catheter, the length of the catheter, and, in some part, the nature of the material from which tube 54 is manufactured. Thus, the closer the catheters are located to the heart, the more conductive the solution in the catheters is, the shorter the catheters are, and the more conductive tube 54 is, the more useful this embodiment will be in performing electrocardiography.

Figure 7:
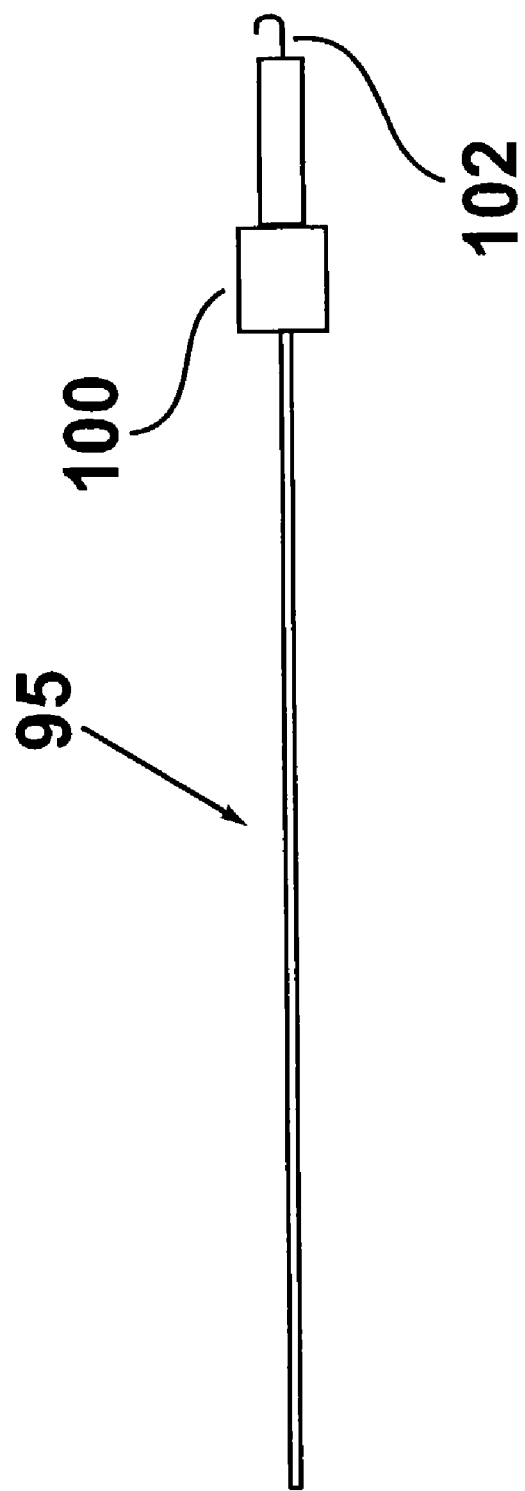
FIG. 7 shows a diagrammatic view of a flexible wire that can be used with the embodiments of FIGS. 3–6.

FIG. 7 shows a diagrammatic view of another embodiment of flexible wire 56 that can be used in any of the test leads described in FIGS. 3–6. As shown in FIG. 7, the first and second test leads can have a flexible wire 95 that comprises a standard electrical probe 100 at its first end. Standard electrical probe 100 has a spring clip 102 that connects flexible wire 56 to hollow tube 54. Flexible wire's 95 second end is connected to ECG monitoring device 41 in the same manner as already described. While electrical probe 100 can be used in association with any of the embodiments of the test leads described in FIGS. 3–6, it will be appreciated by one skilled in the art that the electrical probe's use may not be as effective in circumstances where the animal is very active.

Figure 8:
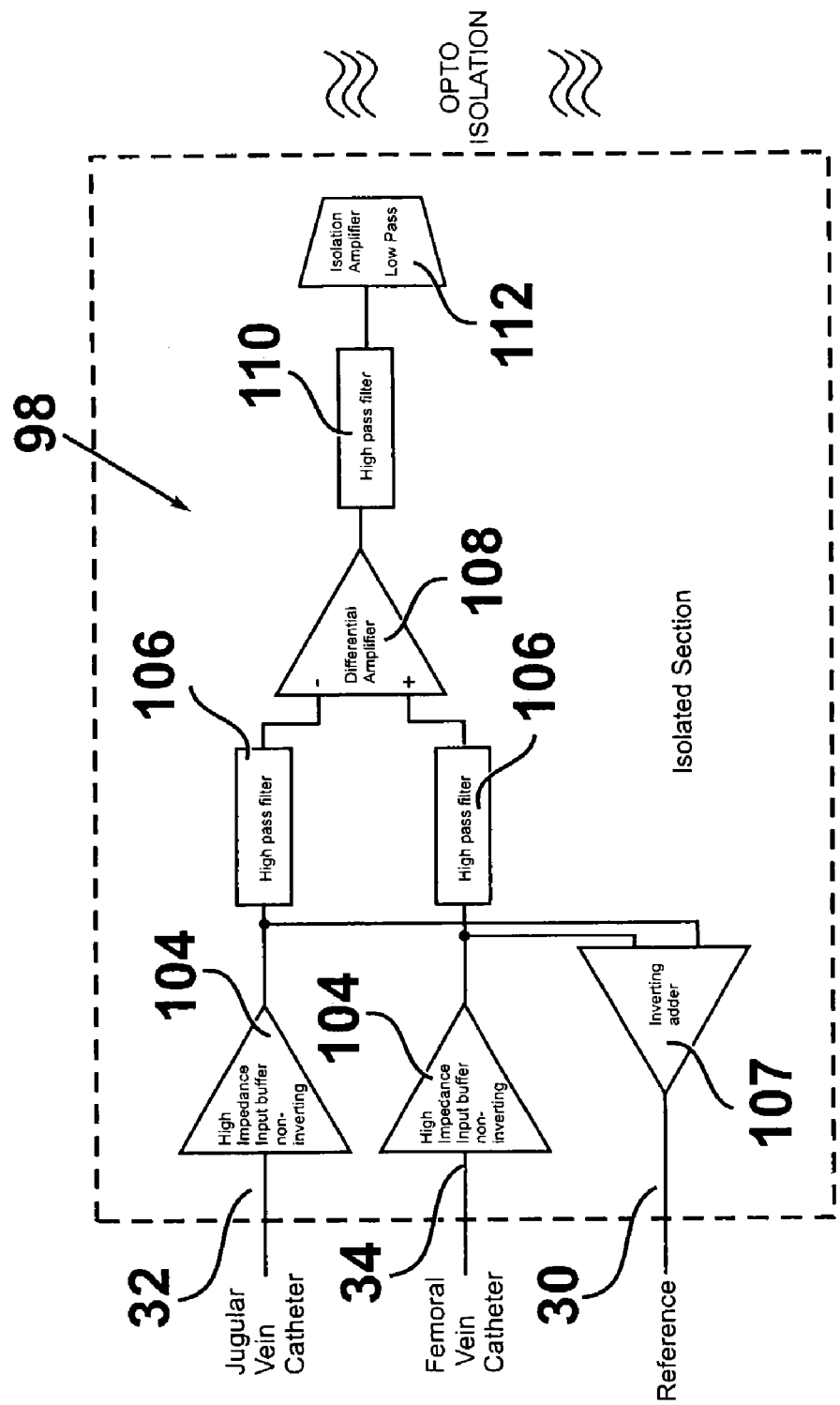
FIG. 8 shows a schematic diagram of one embodiment of the isolated section of the circuit that makes up the present invention.
Figure 9:
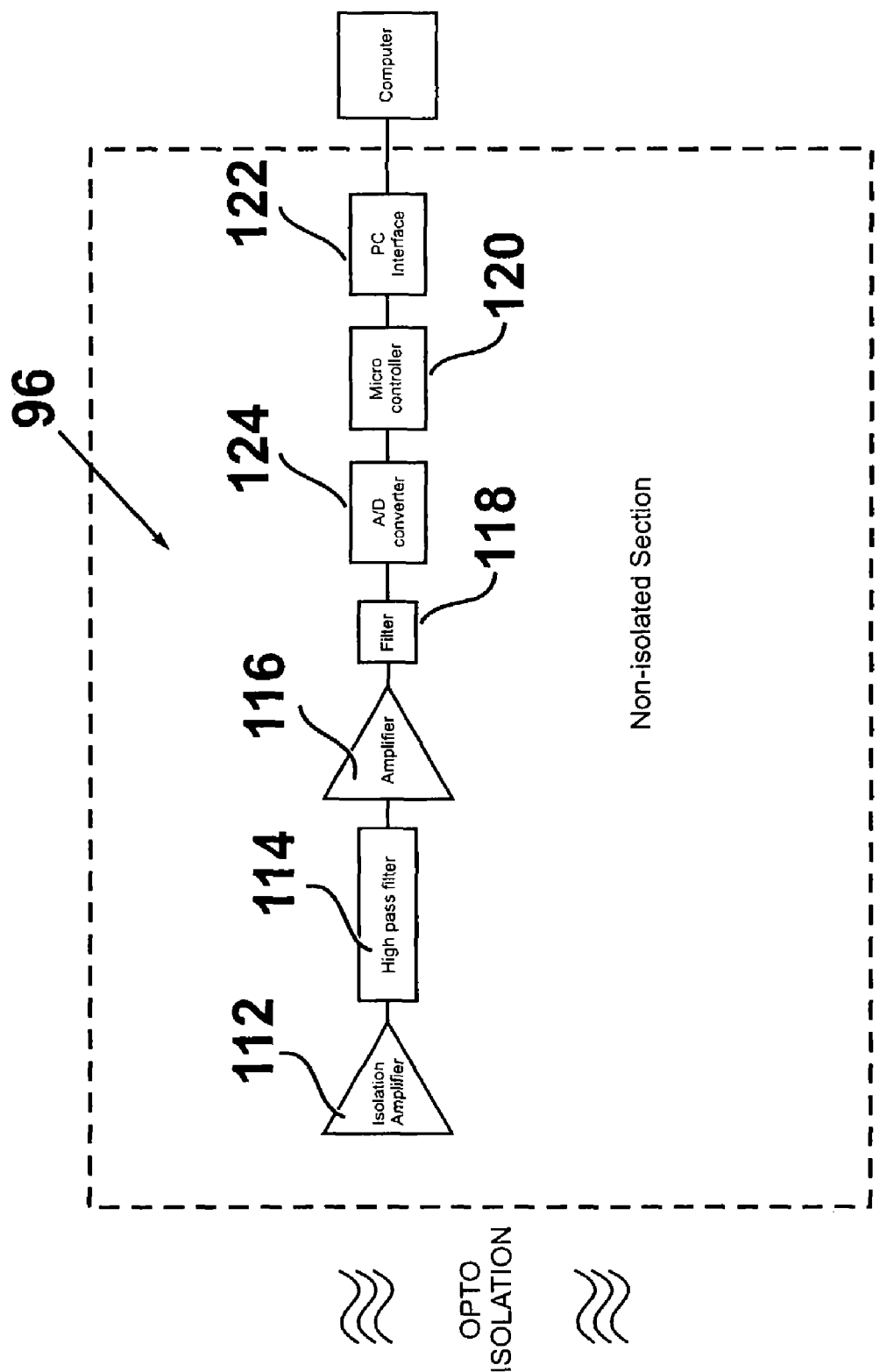
FIG. 9 shows a schematic diagram of one embodiment of the non-isolated section of the circuit that makes up the present invention.

FIGS. 8 and 9 shows a schematic diagram of the circuit of ECG monitoring device 41. FIG. 8 shows a schematic diagram of an isolated section 98 of the circuit. As shown in FIG. 8, isolated section 98 of the circuit is isolated from earth and referenced to the animal to protect the animal from electric shock by an isolation barrier. Starting from the left side and progressing across the schematic, there are three leads, namely, first test lead 32, second test lead 34, and reference lead 30, that connects the animal to ECG monitoring device 41 as previously described. Of these leads, test leads 32 and 34 detect the signal from the heart, while reference lead 30 references the isolated section 98 of the circuit to the animal. Reference lead 30 is electrically connected to an inverting adder 107 in order to reference the reference lead.

Isolated section 98 further comprises two high impedance buffers 104 connected to test leads 32 and 34. High impedance buffers 104 are used because the electrical connections represented by this invention present higher impedance than is typical for electrocardiography. Test leads 32 and 34 make contact with fluid-filled catheters, which are inherently higher impedance conduits than copper wires. Buffers 104 are each electrically connected to inverting adder 107 and a high pass filter 106. High pass filters 106 isolate the DC component of the signal before gain is added. Filters 106 are electrically connected to differential amplifier 108. Differential amplifier 108 takes the difference between the signal leads 32 and 34 and adds gain. Another high pass filter 110 is electronically connected to differential amplifier 108 in order to once again isolate the DC component of the signal. High pass filter 110 is electronically connected to isolation amplifier 112. Isolation amplifier 112 bridges the gap across the isolation barrier to transfer the signal into non-isolated section 96 of the circuit (shown in FIG. 9). During this process, isolation amplifier 112 also effectively acts as a low pass filter to remove high frequency components of the signal. It will be appreciated by one skilled in the art that other combinations of electronic components can be used to achieve the same results. For example, a differential amplifier with a sufficient impedance can replace the high impedance buffers. As another example, there are multiple ways to connect the reference lead and only one of these is illustrated in FIG. 8.

The opto isolation shown in FIGS. 8 and 9 refers to the means by which the isolated section 98 of the electrocardiograph connects to the non-isolated section 96 so that the animal does not receive an electrical shock from electrocardiography device 15. One example of this opto isolation is the use of a light emitting device on the isolated section 98 and a detector on the non-isolated section 96 to provide a connection between the two sections of the circuit. Likewise, this could be achieved with a radiofrequency transmitter on the isolated portion 98 and a receiver on the non-isolated portion 96. Other combinations could include the use of magnetics. The point is to provide a connection that does not involve electric current in order to keep the animal from receiving an electrical shock from the device.

FIG. 9 shows a schematic diagram of non-isolated section 96 of the circuit of the electrocardiograph controller of this exemplary embodiment of the present invention. As shown in FIG. 9, non-isolated section 96 of the circuit further filters and amplifies the signal and then converts the data from analog to digital so that the data can be acquired, stored and displayed on a computer. Isolation amplifier 112 is electrically connected to another high pass filter 114. An amplifier 116 is electrically connected to high pass filter 114 and to a filter 118. High pass filter 114, amplifier 116 and filter 118 further amplify and filter the signal. An A/D converter 124 is electrically connected to filter 118 and to a micro-controller 120. A/D converter 124 converts the data from analog to digital form. Micro-controller 120 is electrically connected to PC interface 122 which interfaces with either local computer 44 or remote computer 46 (shown in FIG. 2).

Micro-controller 120 and PC interface 122 transfer the data to either local computer 44 or remote computer 46 so that the computer can acquire and either store or display the signal. It will be appreciated by one skilled in the art other combinations of electronic components can be used to achieve the same result. For example, the A/D converter could also be used at the beginning of the circuit instead of the end.

Thus, in this embodiment, a modified electrocardiography device is connected to a saline filled jugular vein catheter and to a saline filled femoral vein catheter already installed into a laboratory rat. The connections are facilitated by the use of a hollow metal tube which is located between the catheter and the tubing associated with the blood sampler controller. Such an arrangement still allows programmed drug infusions, or automated blood collection to continue unabated by the process of collecting ECGs from the same animal.

Several designs of this hollow metal tube have been developed. In all cases, it is either necessary to extend the electrical connection from the tube to a point under the rat's skin or to use a connector with electrical properties sufficient to provide a reliable signal. Electrical connection is achieved by the use of a metal extender wire that attaches to the tube or by the modification of the catheter itself to include a metallic coating inside the lumen of the catheter, as long as such coatings are then electrically connected to the tube. In these embodiments, a connection (ground) is made to a surgical staple attached to the rat's skin somewhere on the back. An alternative to the staple and the use of an extender wire or a catheter with a metal coating on the inside, is the use of a catheter with a metal coating on the outside that is isolated from the connecting tube in the catheter and connected to the driven lead. With any of these arrangements, it is possible to record electrical activity from the rat's heart at all times. When the rat is still, resting, sleeping, or otherwise not moving within the confines of its cage, a useful electrocardiogram can be acquired without interference from other muscles in the body.

By devising an interval ranging from seconds to hours, the present invention allows for the recording of electrocardiography activity in an animals heart without human intervention. Since the animal is not moving continuously, it is possible to survey all collected electrocardiography data and select segments of data in which movement artifacts are not present. Referring back to FIG. 2, electrocardiography device 15 permits uninterrupted passage of test leads 32 and 34 from catheters 26 and 28 on rat 20 to ECG monitoring device 41. There is no intervening connection such as an electrical commutator. Yet, rat 20 can still move freely when it wishes to do so because movement responsive caging system 22 detects and compensates for animal movement by turning the cage in a direction opposite to the animal's direction of movement.

During periods when rat 20 moves, the signals obtained from test leads 32 and 34 also record activity from other muscles and no longer reflect heart activity alone. When rat 20 stops moving and rests, electrical activity of the heart can be recorded easily. Because rats are nocturnal, their resting periods coincide with the normal working hours of most humans during the day when most recording will be taking place. Test leads 32 and 34 do not exhibit sensitivity to surrounding instruments and thus can be used in a normal laboratory environment. The operator can view heart activity on a computer screen remote from the laboratory, using a network connection between the computer recording the electrocardiograms and the remote computer. The operator can then determine which segments of the electrocardiograms represent heart activity and process that data through additional filtering and amplification. In this embodiment, extended monitoring can be done over periods of several days without regard to battery life, as no batteries are used or required in this technique.

Thus, exemplary embodiments of the present invention provide for a method of obtaining ECGs from rodents that are conscious and unrestrained. Further, other embodiments provide for a method of obtaining ECGs from larger animals that are conscious, but somewhat restrained. These larger animals are only restrained to the extent reasonably necessary to protect the integrity of the catheters and test leads connected to the animal. Alternatively, a battery powered and portable electrocardiograph can be worn in a backpack by these larger animals. Thus, the device of the present invention does not require that the animal be held in a restraining device and does not require the animal be anesthetized. The present invention thereby eliminates the stress associated with such restraints and eliminates the effect of anesthetics on the ECGs taken from these animals.

Moreover, the method is predicated on the use of two intravenous catheters filled with some electrically conductive, physiological solution that can conduct electrical current. The solution has a chemical composition similar to other body fluids and does not cause harm, pain, distress, or physiological imbalance in the animal. This eliminates the need to use clips or needles to connect test lead wires to the animal. Thus, the present invention eliminates most of the pain and discomfort caused by the connection of test leads to animals. It lessons the time required to prepare an animal for testing by eliminating the need to shave animals, the need to use electrical conductive gels or the need to conduct surgery to implant a device for the purpose of transmitting electrocardiography data. The present invention does not require transmission and reception radiofrequency signals from devices inside or outside of these animals. Thus, animals do not have to be isolated from one another because signal interference from another animal will not be a problem.

The catheters of the invention extend from close proximity to the heart to a point outside the body where they can be connected to test leads. In this manner, the present invention provides for an electrical connection between the monitoring electronics and the electrically conductive solution filled catheter. The present invention provides for a monitoring device capable of overcoming the high impedance inherent in such fluid filled catheters relative to the low impedance situation typically encountered with wire based test leads used in electrocardiography. The present invention provides for at least three leads for the collection of the electrical signals from the fluid filled catheters. One lead for each catheter and a third to be a driven lead connected either to the skin of the animal or connected to an electrically conductive surface on the catheter. The direct connections of the leads and catheters to the animal ensures that the device of the present invention is not sensitive to radiofrequency interference from other devices in the laboratory. Further, because it does not require the use of a battery, the length and frequency of electrocardiography experiments conducted on the animal are not limited by the lifetime of a battery. The present invention does not require that the device be turned on or off by operator intervention in order to obtain a ECG. Thus, it is not limited to intermittent collection of data, but, rather, data collection can be continuous and samples can be taken automatically.

The present invention permits additional monitoring, sample collection, drug infusion, and other tests to be performed on the same animal simultaneously with the collection of the ECGs. Examples of such other tests include automated blood sampling, automated in vivo microdialysis sampling, in vivo ultrafiltration sampling, drug infusions, recording of animal movement, collection of urine and collection of feces. In fact, with the device of the present invention, every one of these additional tests can be conducted in the same animal at the same time. Accordingly, the present invention has the advantage of providing more information from one animal in a single experiment and eliminating individual variation among multiple animals. Therefore, the present invention reduces the number of animals required for a study.

While the subject invention has been described in considerable detail with references to particular embodiments thereof, such is offered by way of non-limiting examples of the invention as many other versions are possible. For example, while all of the embodiments described above have been described in relation to a rat, it will be appreciated by one skilled in the art that the present invention can be utilized in any other animal studies. A study using a pig with catheters positioned in the jugular and saphenous veins would be one such example. It is anticipated that a variety of other modifications and changes will be apparent to those having ordinary skill in the art and that such modifications and changes are intended to be encompassed with the spirit and scope of the pending claims.

We claim:

1. An electrocardiography device for obtaining electrocardiograms from an animal, the device comprising:
   a. first and second intravenous catheters inserted into the animal in close proximity to, but external to, the animal's heart;
   b. at least two test leads, each of the at least two test leads connected to one of the first and second intravenous catheters;
   c. a reference lead;
   d. an electrically-conductive, physiological solution contained in each of the first and second intravenous catheters; and
   e. an ECG monitoring device operatively connected to the at least two test leads and the reference lead.

2. The electrocardiography device of claim 1, wherein the electrically-conductive, physiological solution comprises saline.

3. The electrocardiography device of claim 1, wherein the electrically-conductive, physiological solution comprises Ringer's solution.

4. The electrocardiography device of claim 1, wherein the electrically-conductive, physiological solution comprises blood.

5. The electrocardiography device of claim 1, wherein the electrically-conductive, physiological solution further comprises at least one drug.

6. The electrocardiography device of claim 1, wherein the at least one of the at least two test leads comprises:
   a. a socket connection connected to the ECG monitoring device;
   b. a flexible wire having a first end and a second end, the second end connected to the socket connection;
   c. a hollow tube connected to the first end of the flexible wire and connected to one of the first and second catheters; and
   d. a conductive coating on the outside surface of each of the first and second catheters with the reference lead connected thereto.

7. The electrocardiography device of claim 1, wherein the at least one of the at least two test leads comprises:
   a. a socket connection connected to the ECG nionitoring device;
   b. a flexible wire having a first end and a second end, the second end connected to the socket connection; and
   c. a hollow tube connected to the first end of the flexible wire and connected to one of the first and second catheters.

8. The electrocardiography device of claim 1, wherein the reference lead is connected to the animal.

9. The electrocardiography device of claim 8, wherein the at least one of the at least two test leads comprises:
   a. a socket connection connected to the EGG monitoring device;
   b. a flexible wire having a first end and a second end, the second end connected to the socket;
   c. a hollow tube connected to the first end of the flexible wire and connected to one of the first and second catheters; and
   d. an extender wire placed inside one of the first and second catheters connected to the hollow tube and within the electrically conductive, physiological solution.

10. The electrocardiography device of claim 8, wherein the at least one of the at least two test leads comprises:
    a. a socket connection connected to the ECG monitoring device;
    b. a flexible wire having a first end and a second end, the second end connected to the socket connection;
    c. a hollow tube connected to the first end of the flexible wire and connected to one of the first and second catheters; and
    d. a metal coating on the inside of each of the first and second catheters.

11. The electrocardiography device of claim 1 further comprising a movement responsive caging system for housing the animal.

12. The electrocardiography device of claim 11, further comprising an automated blood controller connected to the first and second intravenous catheters.

13. The electrocardiography device of claim 12, wherein the automated blood controller and the EGG monitoring device comprise a single control device.

14. The electrocardiography device of claim 12, further comprising a computer operatively connected to the automated blood controller.

15. The electrocardiography device of claim 14, wherein the automated blood controller, the ECG monitoring device, the output device, and the computer all comprise a single device.

16. The electrocardiography device of claim 14, further comprising an output device for displaying an electrocardiogram from the EGG monitoring device.

17. The electrocardiography device of claim 16, wherein the output device comprises a printer.

18. The electrocardiography device of claim 16, wherein the output device comprises a display screen.

19. The method for obtaining an electrocardiogram from an animal, the method comprising the steps of:
    a. providing an ECG monitoring device, a first catheter and a second catheter, a reference lead, and at least two test leads;
    b. connecting at least one of the at least two test leads to the first catheter and the ECG monitoring device;

c. connecting the other of the at least two test leads to the second catheter and the ECG monitoring device, and connecting the reference lead to the animal and the ECG monitoring device;

d. inserting the first catheter into the a first vein near the animal's heart, and inserting the second catheter into a second vein near the animal's heart so that the first and second catheters are located on a axis running diagonally across the heart from on of the heart's atriums to a position just below the opposite ventricle of the heart;

e. filling the first catheter and the second catheter with an electrically conductive, physiological solution; and f. processing a plurality of signals received from the at least two test leads with the ECG monitoring device to produce an electrocardiogram.

20. The method of claim 19, further comprising the step of adding at least one drug to the electrically-conductive, physiological solution as a continuous stream of fluid in order to test the effects of the drug on the animals heart.

21. The method of claim 19, further comprising the step of adding at least one drug to the electrically-conductive, physiological solution as a bobs stream of fluid in order to test the effects of the drug on the animal's heart.

22. The method of claim 19, wherein the at least one of the at least two test leads comprises:
  a. a socket connection connected to the ECG monitoring device;
  b. a flexible wire having a first and second end, the second end connected to the socket connection;
  c. a hollow tube connected to the first end of the flexible wire and connected to one of the first and second catheters; and
  d. an extender wire placed inside one of the first and second catheters and the electrically-conductive, physiological solution, such that the extender wire collects the plurality of signals that the ECG monitoring device uses to produce the electrocardiogram.

23. The method of claim 19, wherein the at least one of the at least two test leads comprises:
  a. a socket connection connected to the ECG monitoring device;
  b. a flexible wire having a first and second end, the second end connected to the socket connection;
  c. a hollow tube connected to the first end of the flexible wire and connected to one of the first and second catheters; and
  d. a metal coating on the inside of each of the first and second catheters, such that the metal coatings collects the plurality of signals that the ECG monitoring device uses to produce the electrocardiogram.

24. The method of claim 19, wherein the at Least one of the at least two test leads comprises:
  a. a socket connection connected to the ECG monitoring device;
  b. a flexible wire with a first and second end, the second end connected to the socket connection;
  c. a hollow tube connected to the first end of the flexible wire and connected to one of the first and second catheters; and
  d. a conductive coating on the outside surface of cach of the first and second catheters with the reference lead connected to this outside surface instead of the animal, such that the conductive coating collects the plurality of signals that the ECG monitoring device uses to produce the electrocardiogram.

25. The method of claim 19, wherein the at least one of the at least two test leads comprises:
  a. a socket connection connected to the ECG monitoring device;
  b. a flexible wire with a first and second end, the second end connected to the socket connection; and
  c. a hollow tube connected to the first end of the flexible wire and connected to one of the first and second catheters, such that the hollow tube collects the plurality of signals that the ECG monitoring device uses to produce the electrocardiogram.

26. An electrocardiography device for obtaining electrocardiograms from an animal, device comprising:
  a. two intravenous catheters connected to the animal in close proximity to, but external to, the animal's heart;
  b. an electrically conductive, physiological solution contained in each of the two catheters;
  c. an ECG monitoring device, and
  d. a means for providing an electrical connection between the electrically-conductive, physiological solution and the ECG monitoring device.

* * * * *